(12) United States Patent
Cao

(10) Patent No.: US 7,141,369 B2
(45) Date of Patent: Nov. 28, 2006

(54) MEASURING CELLULAR METABOLISM OF IMMOBILIZED CELLS

(75) Inventor: Bo Cao, Shanghai (CN)

(73) Assignee: Semibio Technology, Inc., Florham Park, NJ (US)

( * ) Notice: Subject to any disclaimer, the term of this patent is extended or adjusted under 35 U.S.C. 154(b) by 0 days.

(21) Appl. No.: 10/132,543

(22) Filed: Apr. 25, 2002

(65) Prior Publication Data
US 2003/0203365 A1 Oct. 30, 2003

(51) Int. Cl.
C12Q 1/68 (2006.01)
C12N 11/16 (2006.01)
G01N 15/06 (2006.01)
B32B 17/00 (2006.01)

(52) U.S. Cl. .................. 435/6; 435/174; 435/283.1; 422/68.1; 428/410

(58) Field of Classification Search .................. 435/6, 435/7.1, 174, 283.1; 422/68.1; 530/300, 530/387.1
See application file for complete search history.

(56) References Cited

U.S. PATENT DOCUMENTS

| 4,357,142 A | 11/1982 | Schall, Jr. et al. |
| 4,591,570 A | 5/1986 | Chang |
| 4,677,061 A | 6/1987 | Rose et al. |
| 4,952,519 A | 8/1990 | Lau |
| 5,066,582 A | 11/1991 | Tsuruta et al. |
| 5,100,777 A | 3/1992 | Chang |
| 5,208,111 A * | 5/1993 | Decher et al. ............. 428/420 |
| 5,246,832 A | 9/1993 | Michelson et al. |
| 5,340,719 A | 8/1994 | Hajek et al. |
| 5,348,859 A | 9/1994 | Brunhouse et al. |
| 5,554,505 A | 9/1996 | Hajek et al. |
| 5,556,760 A | 9/1996 | Nakamura et al. |
| 5,602,042 A | 2/1997 | Farber |
| 5,643,721 A * | 7/1997 | Spring et al. .................. 435/6 |
| 5,658,732 A * | 8/1997 | Ebersole et al. ............... 435/6 |
| 5,658,745 A | 8/1997 | Greene et al. |
| 5,674,696 A | 10/1997 | Nakamura et al. |
| 5,711,915 A | 1/1998 | Siegmund et al. |
| 5,716,854 A | 2/1998 | Lofas et al. |
| 5,866,350 A | 2/1999 | Canavaggio et al. |
| 5,879,951 A | 3/1999 | Sy |
| 5,880,835 A | 3/1999 | Yamazaki et al. |
| 6,017,496 A * | 1/2000 | Nova et al. ................. 422/68.1 |
| 6,025,126 A | 2/2000 | Westbrook |
| 6,063,637 A | 5/2000 | Arnold et al. |

(Continued)

FOREIGN PATENT DOCUMENTS

EP 0 223 978 8/1992

(Continued)

OTHER PUBLICATIONS

JP Patent Abstract No. 04056250 published on Aug. 24, 1993.

(Continued)

*Primary Examiner*—B J Forman
(74) *Attorney, Agent, or Firm*—Michael J. Wise; Perkins Coie LLP (57) ABSTRACT

This invention uses a receptor molecule such as an antibody etc immobilized to a chip for a solid phase, and a sensor such as a pH electrode or an oxygen electrode or a glucose electrode for a search device. After immobilizing specific living cells by a bio-specific recognition reaction (a special immunity bond reaction) and washing the solid phase chip, one can measure the change of pH or oxygen consumption or glucose consumption from the metabolism of the specific living cells in substrate solution. This makes it possible to measure the activity and quantity of living cells specifically, accurately and quickly.

14 Claims, 8 Drawing Sheets

Image of Measurement Principle

This is a schematic diagram of the present method for measuring the activity and quantity of living cells. After absorbing with specific living cells by a specific binding reaction and washing the solid phase chip, the change of pH from the metabolism of the specific living cells can be measured by pH-FET sensor.

U.S. PATENT DOCUMENTS

| | | | |
|---|---|---|---|
| 6,132,961 | A | 10/2000 | Gray et al. |
| 6,303,325 | B1 | 10/2001 | Mehta et al. |
| 6,379,910 | B1 | 4/2002 | Nakamura et al. |
| 6,461,825 | B1 | 10/2002 | Carriere |
| 6,689,478 | B1 * | 2/2004 | Laguitton ............ 428/441 |
| 6,766,817 | B1 | 7/2004 | da Silva |
| 2001/0041347 | A1 * | 11/2001 | Sammak et al. ........ 435/7.23 |
| 2002/0076833 | A1 | 6/2002 | Henry et al. |
| 2002/0192676 | A1 | 12/2002 | Madonna et al. |
| 2004/0009471 | A1 | 1/2004 | Cao |

FOREIGN PATENT DOCUMENTS

| | | |
|---|---|---|
| WO | WO 88/07201 | 9/1988 |
| WO | WO 01/11362 | 2/2001 |
| WO | WO 03/091394 A2 | 11/2003 |
| WO | WO 03/091394 A3 | 11/2003 |

OTHER PUBLICATIONS

JP Patent Abstract No. 06243778 published on Apr. 30,1996.
Kam et al., Clin. Diagn. Lab. Immunol: 3(3):326-330.
Pascale et al., Clin. Diagn. Lab. Immunol: 4(4):474-477.
Kannangai et al., Clin. Diagn. Lab. Immunol: 8(6):1286-1288.
Documents from http://www.affordcd4.com.
Abstract: Greenberg et al., Blood 65(1):190.
Abstract: Randall, J Immunol Methods, 60(1-2) 147.
Abstract: Morhenn et al., JID 81:127s.
Abstract: Wood et al., JID 84(I):37.
Abstract: Bundesen et al., J Immunol Methods 30(2):179.
Abstract: Nash, J Immunol Methods 12(1-2):149.
Abstract: Vakkila et al., Immunol Lett (15(3):229.
Abstract: Bash et al., J Immunol Methods 56(3):269.
Abstract: Tsoi et al., J Immuno Methods 53(3):293.
Abstract: Ralph et al., Stem Cells 2(2):88.
Abstract: Smedman et al., Am J Trop Med Hyg 41(1):116.
Abstract: Burgess et al., J Immunol Methods 227(1-2):169.
Abstract: Morecki et al., J Biol Response Mod 9(5):463.
Abstract: Larsson et al., J Immunol Methods 116(2):293.
Abstract: Gomez et al., 15(2):238.
Abstract: Pope et al., 28(4):449.
Abstract: Gee et al., J Immunol Methods 142(1):127.
Abstract: Nordon et al., Cytometry 16(1):25.

* cited by examiner

FIG.1

This is a schematic diagram of the present method for measuring the activity and quantity of living cells. After absorbing with specific living cells by a specific binding reaction and washing the solid phase chip, the change of pH from the metabolism of the specific living cells can be measured by pH-FET sensor.

PEI+PSS+PLL+BNHS+
Biotin-CD4+FITC-anti-
Mouse IgG (washed)

PEI+PSS+PLL+BNHS+
Stav+Biotin-CD4+FITC-
anti-Mouse IgG (washed)

MEASURING CELLULAR METABOLISM OF IMMOBILIZED CELLS

BACKGROUND OF THE INVENTION

1. Field of the Invention

The measurement of cell activity and cell quantity is important in all fields of biotechnology and life sciences.

In the early stages of a disease, such as inflammation, cell activity has already changed before the change in cell quantity. Instead of current diagnosis methods that measure cell quantity, the present invention can directly measure cell activity, and provides a better method for early clinical diagnosis. Because it is highly sensitive, the present invention also can be used for in vitro diagnostics for cancer, autoimmune, metabolic and genetic diseases. In addition, the present invention provides an easy and inexpensive method for detecting the fixed-quantity of CD 4+ cell in whole blood to help the diagnosis of AIDS and HIV infected patients. This invention not only has implications in clinical diagnosis, but also in drug development, pharmacy research, new chemical compounds research, toxicological and environmental testing. This invention has immediate commercial applications for testing cellular health as a quality control tool for cellular medicine.

2. The Prior Art

In order to measure cell activity, the products of cell metabolism can be measured in various ways. Acids can be detected by the change in color of a pH indicator inserted in the culture solution, and gas can be detected by the Wallbulck's gas measure. The quantity of the oxygen in a cell culture medium will decrease with the cell metabolism, and putting an oxygen electrode into the cell culture medium is a way to measure cell activity in real-time [I. Karube, T. Matsunaga, S. Mitsuda, S. Suzuki: Biotechnol. Bioeng., 19, 1537 (1977)].

Additionally, methods such as enzyme assays, electrochemistry assays, and chemistry fluorescence emission assays are used for testing cell activity. For example, the impedance method detects electric change directly as cell metabolism activity [P. Cady, S. Dofour, P. Lawless, B. Nunke, and S. Kraeger, J. Clin. Microbiol., 7, 273, (1978)]. The conductance method depends on the same principle of impedance method [J. Richard, A, Jason, G. Hobbs, D. Gibson, and R. Christie, J. Phys. E. Sci. Instrum., 11, 560, (1978)]. The composition enzyme substrate solution method detects the quantity of the color emission or the fluorescence emission of the isolated chemical compound as enzymatic activity [M. Manafi, and W. Kneifel, Acta Microbial. Hungarica 38, 293, (1991)]. The bioluminescence method detects the quantity of the ATP that is a product of cell metabolism [W. McElroy, H. Seliger, and E. H. White, Photochem. Photobiol., 10, 153, (1969)].The LAPS method provides a method wherein the rate of production of living cells acidic metabolites could be measured continually by a light-addressable potentiometric sensor. [J. Parce, John C. Owicki, M. Kercso, Science., 5, 243, (1989)]

Evaluation of the activity of living cells using cytotoxicity measurements is important for assessing the effect of drugs, environmental pollutants, temperature and ionic extremes, radiation and irradiation, other cells and biological modifiers and other potentially adverse factors on cells and tissues.

One such cytotoxicity measurement is a DNA assay which depends on a fluorescent dye. Growing living cells are dyed by 2-diamidino-phenylindole (DAPI) or Hoechst 33342, which is a fluorescent dye. The fluorescence intensity of the resulting dyed cells is measured by a fluorescence photometer. Cells are placed in the holes of a 96-hole microtiter plate together with culture fluid and cultured for 2 days in a 37.degree. C. carbon dioxide incubator. After the culture fluid has been replaced with a new culture fluid containing a chemical substance to be tested, the chemical substance acts on the cells for 3 days. Subsequently, the culture fluid is discharged, and then the cells are fixed by a glutaraldehyde solution. Thereafter, the cells are dyed by DAPI or Hoechst 33342 solution. The fluorescence intensity of the resulting dyed cells is measured by a photometer. Finally, the cell density is determined on the assumption that control fluorescence intensity is 100%

Another cytotoxicity testing method uses MTT ([3-(4, 5-dimethylthiazol-2-yl)-2, 5-diphenyl tetrozorlium bromide]). MTT produces formazan due to an enzyme present in intracellular mitochondria. After formazan has been dissolved in hydrochloric acid-isopropanol, calorimetric quantization is effected. The amount of formazan is dependent on the number of live cells and therefore representative of the same. Cells, a culture fluid and a chemical substance solution to be tested are introduced into the holes of a 96 hole microplate and cultured for 24 hours in acid-isopropanol solution, and black crystals of formazan are dissolved by stirring. The degrees of absorption of 570 nm light and 630 nm light are determined by a microplate reader in order to quantize the toxicity of the chemical substance.

Sup 51 Cr take-in method is also used in cytotoxicity testing. While the 51Cr isolation method is effective with chemical substances of the kind inducing cytolytic-death in a short period of time, it is insensitive to substances of the kind that do not not fully destroy cell walls. The. sup.51 Cr take-in method is an improved version of the. sup.51 Cr isolation method as to its ability to decide whether cells are live or dead. Specifically, after a cell solution has been introduced in the holes of a 96-hole microplate, a chemical substance solution to be tested is added. The plate is held at 37.degree. C. for 1 hour to 8 hours, and then the top of the solution is removed by a centrifugal force. A culture fluid containing 1.Ci of Na.sub.2.sup.51 CrO.sub.4 is introduced into the holes of the plate and held at 37.degree. C. for 30 minutes. After .sup.51 Cr not taken into the cells has been fully discharged, 50.1 of acetic acid is added to each hole and fully stirred. All the contents of the holes are transferred to gamma counter tubes in order to measure their radioactivity.

In all of these above-mentioned methods, it takes a long time to culture living cells. Usually, cultured cells form irregular colonies in which cells high in activity and growth ability and cells low in the same exist together. Only cell concentrations above $10^6$ cells/Ml can be detected using these methods. In addition, all of these methods require skill and complicated operations as well as expensive apparatus for determination. Furthermore, as they are sometimes inaccurate and insensitive, these methods are not suitable for clinical diagnosis.

The most useful method for detecting the activity and the quantity of living cells is flow cytometry. Flowcytometers generally are characterized as having one or more sources of excitation (typically lasers tuned to a specific frequency), means which allow the passage of cells substantially one at a time through a measurement region and means for detection of light scatter and fluorescence from cells as they pass through the measurement region. Means to record the data for each of the cells also may be coupled to the device. For example, a Trypan Blue solution is added to a cell solution, and only dead cells take it up. Trypan Blue absorbs red helium-neon laser light having a wavelength of 632.8 nm and issuing from a flowcytometer. Therefore, a sample consisting of a number of cells is instantaneously divided into three groups of spots, i.e., living cells, dead cells, and cell fractions. The three groups of spots are drawn on an oscilloscope and allow a ratio between living cells and dead cells to be easily determined. When Hoechst 33342 and propidium iodide are used to dye DNA of unfixed cells, activity unchanged living cells and activity injured cells fluoresce in blue and red, respectively and can therefore be easily distinguished by a flowcytometer. With fluorescence-coated monoclonal antibody, the quantity of cells also can be measured by flowcytometry. The fixed-quantity measurement of CD 4+ cell in whole blood is a test that is necessary for AIDS and HIV infected patients. However FCM is an expensive and complex measurement. 90% of AIDS and HIV infected patients in the world can't have the fixed-quantity measurement of CD 4+ cell currently. In addition it is difficult to fix specific cells and a sufficient amount of sample is necessary for this test.

SUMMARY OF THE INVENTION

This invention provides an improved method for assessing the activity and quantity of living cells which is accurate and easy and occurs in real-time. Using charged polyion binding or chemical reaction bonding or covalent bonding, an antibody reacting with various proteins exposed on the surface of cells, a ligand molecule reacting with various receptors exposed on the surface of cells or partial peptide thereof, or a receptor reacting with various cell adhesion factors exposed on the surface of cells or partial peptide thereof is immobilized on the inner surface of the capillary chip as a solid phase. After a bio-specific recognition reaction (a special immunity bond reaction) and washing the solid phase chip with substrate solution, specific living cells can be immobilized on the inner surface of the solid phase chip. As living cells are dipped in the substrate solution including some culture ingredients like glucose, it is possible to measure the change of pH or oxygen consumption or glucose consumption from the metabolism of the specific living cells by a sensor such as a pH electrode or an oxygen electrode or a glucose electrode. This also means it is easily possible to measure the activity and quantity of living cells specifically, accurately and quickly with the present invention.

This invention also provides a method for immobilizing specific living cells on a solid phase chip. Further, this invention provides a method for determining the quality of a receptor-molecule solid phase chip.

Additionally, this invention provides a chip for measuring the activity or quantity of living cells. This invention also provides an apparatus for measuring the activity and quantity of cells.

DETAILED DESCRIPTION OF THE INVENTION

Referring to FIGS. 1–8 of the drawings, the present invention provides for a receptor molecule solid phase chip for immobilizing specific living cells, an apparatus for a bio-specific recognition reaction between specific living cells and a receptor molecule solid phase chip, an apparatus for the determination of the activity and quantity of specific living cells and an apparatus for the evaluation (observation) of specific living cells morphology and quantity.

The receptor molecule solid phase chip may be made of a polyolefin polymer such as polystyrene, polyethylene, polypropylene and the like, a polyester polymer such as polyethylene terephthalate, polybutylene terephthalate and the like, a polyamide polymer such as nylon 6, nylon 6.6 and the like, and a polycarbonate, cellulose polymer such as cellulose acetate, nitrocellulose and the like.

Since the receptor molecule solid phase chip is used to measure the change of pH or oxygen consumption or glucose consumption from the metabolism of the specific living cells, the chip is be made of materials that do not absorb carbon dioxide, oxygen and other materials that may disturb the accuracy of the determination of the activity and quantity of specific living cells. It is desirable that the receptor molecule solid phase chip used is composed of glass, quartz glass, other glasses such as Li niobate, zinc selenide, porcelain, semiconductor materials such as germanium, GaAs or silicon, and metals such as aluminium, or steel.

In order to provide the chip wherein a small quantity of the sample may be used, and one that is inexpensive and easy to use to carry out the measurement, it is desirable that the solid phase chip be composed of one with a short capillary with narrow diameter. The inner surface of the short capillary with narrow diameter is used as the solid phase.

After a bio-specific recognition reaction (a special immunity bond reaction), specific living cells can be immobilized on the inner surface of the receptor molecule solid phase chip. The bio-specific recognition reaction (special immunity bond reaction) is generally based on the ability of a receptor molecule recognizing specifically the structure and molecular organization of a ligand molecule on the surface of specific living cells, for example of an antibody reacting with various proteins exposed on the surface of cells, a ligand molecule reacting with various receptors exposed on the surface of cells, or a receptor reacting with various cell adhesion factors exposed on the surface of cells, and to bind this molecule on the surface of cells very specifically in such a manner (see FIG. 1).

To immobilize a receptor molecule on the inner surface of the chip, several binding methods based on ionic linkages, covalent bonds, hydrogen bonds and van der Waals forces may be used. For example the physical adsorbing method, ionic binding method, chemical binding method and so on. Furthermore, in the present invention, biotinylated compounds adsorbing method, aminosilane coupling method and polyions charged method may be suitable and effective.

According to the biotinylated compound adsorbing method, biotinylated compounds with a large molecular weight such as biotinylated bovine serum albumin (BSA) may be used. After washing the chip with water in an ultrasound bath, the chip is treated with 0.01 and 1 mg/ml biotinylated-BSA over night. Due to van der Waals forces, biotin-BSA is strongly immobilized on the inner surface of the chip. Then, as pair biotin/avidin is a very effective and strong covalent bonder, using a sandwich binding method with streptavidin and biotinylated antibody and the like, a receptor molecule recognizing specifically the structure and molecular organization of a ligand molecule on the surface of specific living cells can be immobilized on the inner surface of the chip.

According to the aminosilane coupling method, a capillary that is made of glass or quartz is treated with alkali liquor or acid and washed with water in an ultrasound bath and carefully dried with nitrogen gas, which cleans the surfaces and makes them dust-free.

After reacting with the aminosilane such as 3-aminopropyltriethoxysilane, 3-aminopropyldimethylethoxysilane and so on, and treating with a glutaraldehyde aqueous solution, amino group is loaded onto the surface of the capillary via the silane reaction. Finally, reacting with the receptor molecule such as an antibody, or peptide directly, the receptor molecule recognizing specifically the structure and molecular organization of a ligand molecule on the surface of specific living cells can be immobilized on the inner surface of the chip with a peptide bond.

Furthermore, as pair biotin/avidin provides a very effective and strong covalent bond, using a sandwich binding method, such as biotinylated bovine serum albumin (BSA)/streptavidin/biotinylated antibody, a receptor molecule recognizing specifically the structure and molecular organization of a ligand molecule on the surface of specific living cells can be immobilized on the inner surface of the chip too.

According to the polyion charged method, which is the preferred embodiment of the invention, polyanions and polycations are required as adsorbing polyions. Suitable and preferred polycations are compounds with amino groups, such as polylysine, polyallylamine, polyvinylpyridine, dextrans modified with amino groups (for example DEAE-dextran), and chitosan. Suitable and preferred polyanions are polycarboxylic acids and polysulphonic acids. Examples of these are polyglutamate, polystyrenesulphonic acid, or dextran sulphate (see FIG. 2).

Furthermore, on glass or quartz, it is possible to adsorb polycations, such as polyethyleneimine, after briefly dipping it into water or sodium hydroxide solution. The construction of the inner surface of the solid phase chip can take place by successively alternating immersion of the support in aqueous solutions which contain polyions, for example polycations, polyanion, polycation, and so on, with rinsing processes carried out in between. Due to the opposite charge binding, the polyanion layers and polycation layers alternate with respect to each other.

When polyions are applied, they bind horizontally and thus prevent a loss of potential binding sites in the layer below. This is additionally favoured by the fact that no discrete covalent bonds are formed, but, as a result of the electrostatic forces, a spatially fixed assignment of the ions on the various layers is not required.

The polyions are preferably dissolved in concentrations between 1 and 100 mg/ml in the solvent, the optimum concentration depending on the molecular weight and the nature of the coating technique used and needing to be optimized in the individual case.

After the toplayer is coated using polylysine as a polycation, the chip reacts with the activated biotin active ester (biotin N-hydroxysuccinimide=BNHS) using triethylamine as a pH adjuster for at least more than 4 hours. A suitable solvent of the activated biotin active ester contains cyclic amides, such as dimethylformamide, dimethylacetamide, N-methylpyrrolidone and others. Since peptide bonds are formed the, biotin molecule is strongly immobilized onto the polylysine that is the toplayer of the chip.

Finally, as pair biotin/avidin provides a very effective and strong covalent bond, using a sandwich binding method, such as biotin/streptavidin/biotinylated antibody, a receptor molecule recognizing specifically the structure and molecular organization of a ligand molecule on the surface of specific living cells is immobilized on the inner surface of the chip.

The process of polyion charged binding for producing the receptor molecule solid phase chip can easily be converted into a continuous procedure by passing the modified support to be coated in succession through various immersions. This reduces the amount of work considerably, compared with the other binding methods.

The quality control of the production of the receptor molecule solid phase chip, for example testing whether the receptor molecule is immobilized on the inner surface of chip or whether the homogeneity of the each different layer of the solid phase is good, is very important in the process of producing the receptor molecule solid phase chip.

Such testing may be done by the convenient fluorescence emission method. After reacting with varieties of fluorescence-labelled chemical agents such as fluorescence-labelled polyanions, fluorescence-labelled polycations, fluorescence-labelled streptavidin, fluorescence-labelled biotin, fluorescence-labelled antibody and so on, fluorescence-labelled chemical agents can be adsorbed with each different layer of the solid phase, and the quantity of the fluorescence emission can be detected with a UV transilluminator and charge coupled device (CCD) camera.

Furthermore, suitable conditions for producing the receptor molecule solid phase chip such as concentration of the reaction agents, reaction temperature, reaction time and so on, can be confirmed by the convenient fluorescence emission method. It is convenient, specific, effective and low cost, compared with the other testing methods.

A normal bio-specific recognition reaction requires only immersing the receptor molecule solid phase chip in a sample including specific living cells such as cell soliquoid. However, when the sample involved contains whole blood, an apparatus for a bio-specific recognition reaction between specific living cells and a receptor molecule solid phase chip is necessary to be used to prevent corpuscle subsidence.

The apparatus for a bio-specific recognition reaction consists of a micropump that supplies the sample including specific living cells to throw chips, and narrow diameter pipes that connect with the micropump and chips.

A suction method may be used to supply the sample throwing chips with a perista pump, a syringe pump or a suction pump. In addition, a supplying rate of 1 to 100 l/min is suitable and enough for doing a bio-specific recognition reaction fully, and the pipes may be made of silicon tubes, rubber tubes and so on.

Figure 1:
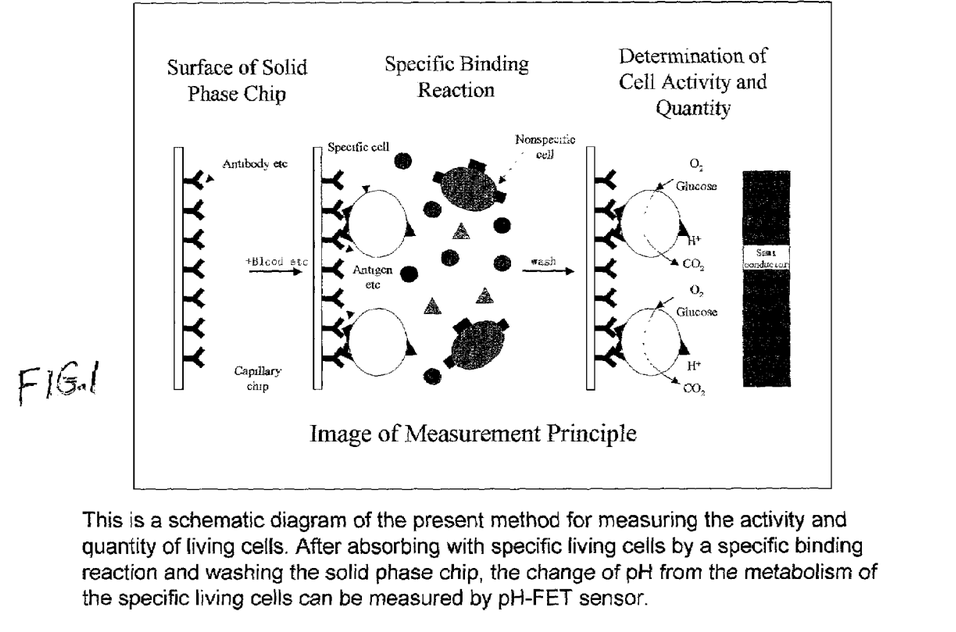
FIG. 1 is a schematic diagram of the present method for measuring the activity and quantity of living cells.
Figure 2:
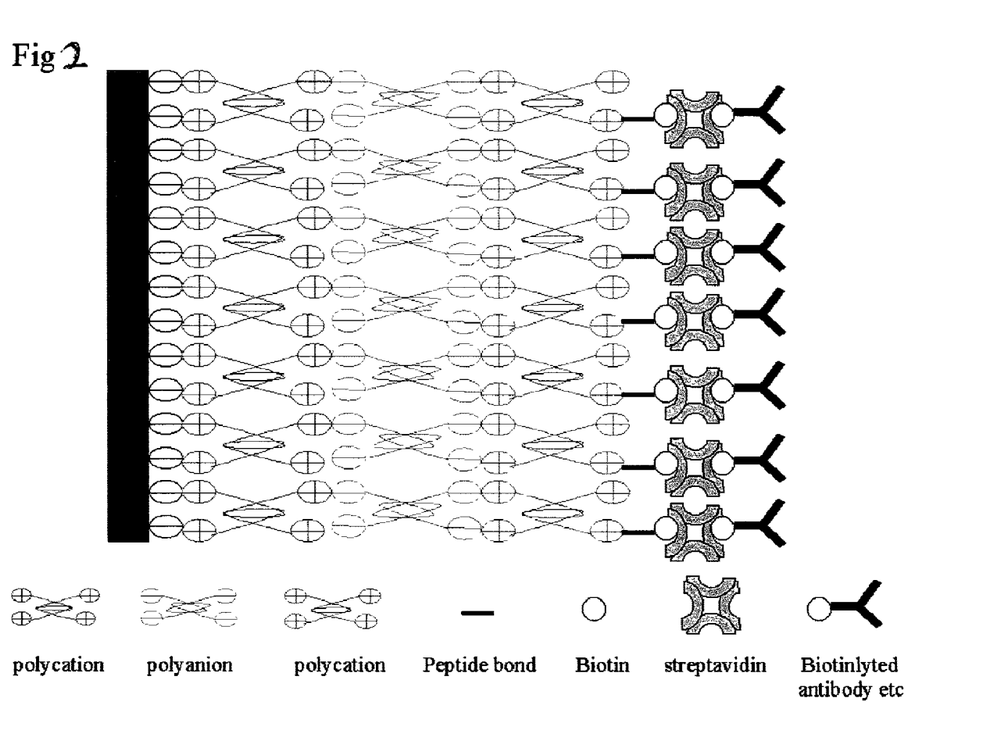
FIG. 2 is a schematic diagram of the method for making the solid phase chip using charged polyion binding and chemical reaction binding.
Figure 3:
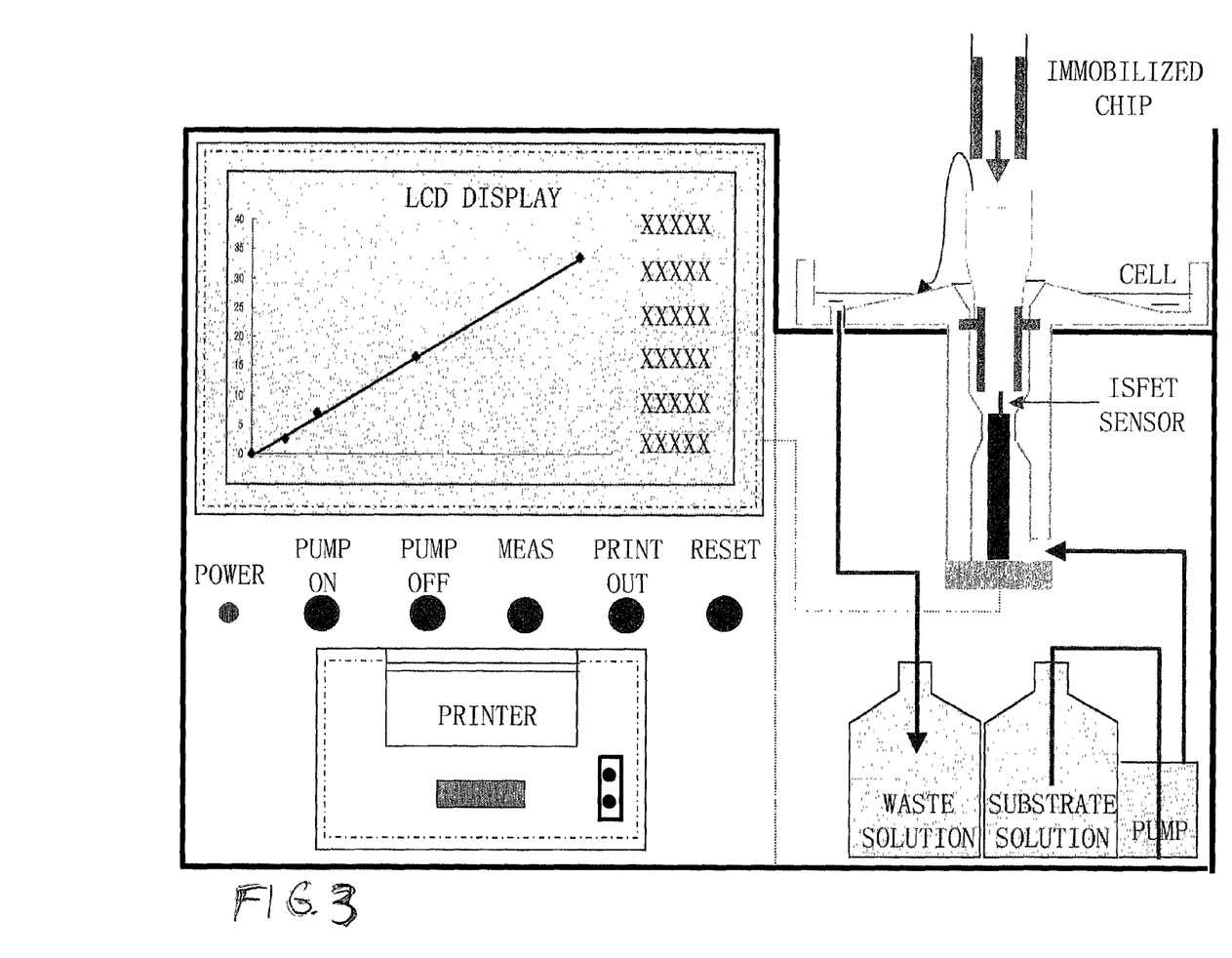
FIG. 3 is a schematic diagram of one preferred embodiment of the apparatus of the present invention for measuring the activity and quantity of living cells.

The apparatus for the determination of the activity and quantity of specific living cells consists of a cell having an inlet and outlet for the substrate solution, a sensor accommodated in the cell which can measure the change of pH or oxygen consumption or glucose consumption from the metabolism of the specific living cells, a pump for supplying the substrate solution and antiseptic washing solution in the cell, a liquid reservoir for pooling a substrate solution, a reference electrode of the sensor in the liquid reservoir, a circuit for activating the sensor, and a means for controlling the action of the pump and reading and displaying the signal from the sensor (see FIG. 3).

To measure the change of pH or oxygen consumption or glucose consumption from the metabolism of the specific living cells, the above-mentioned sensor applies to a pH electrode, an oxygen electrode and a glucose electrode.

According to the pH electrode, a pH sensitive field-effect transistor (pH-FET) has excellent characteristics such as: (1) it may easily be reduced in diameter; (2) it has a low amount of induced noises when reduced in diameter; (3) since it is prepared by IC techniques, the scatter of properties between electrodes can be made small and its pH sensitive plane (gate part) can be made very small; (4) it has an extremely rapid response to a pH change and has no remnant hysterisis in the response curve; (5) it has a wide linear region responsive to a pH change; and (6) it has a semipermanent life when stored in water and small change in properties such as the pH sensitivity over a period of time. Therefore, the pH-FET is most suitable for a pH electrode employed in the present invention.

It is desirable that the pH-FET employed in the present invention have a pH sensitivity of 40 to 60 mV/pH, preferably 50 to 60 mV/pH at 25.degree. C.

In addition, it is desirable that the leakage current is not higher than 10 nA when 1.5 V of the voltage is applied between a source electrode of the pH-FET and an outer electrode while soaking the tip part of the elemental device of the pH-FET and an outer electrode in a physiological sodium chloride solution.

In order to improve the measuring accuracy by suppressing the influence of drift due to various factors, a liquid holding part is provided to the tip end of the thin tube to keep a substrate solution communicating with the pH-ISFET, then another pH-ISFET for reference and pusedo comparison electrode are fitted to the liquid holding part.

According to the position of the sensor, the detection part of the sensor is provided in the cell measurement is adjacent to one end of the acceptor molecule solid phase chip or inserted into the inner of the acceptor molecule solid phase chip.

On the other hand, with thermostatical control such as constant temperature water bath or constant temperature atmosphere bath and like, the temperature of the above-mentioned cell is thermostatically controlled to be 37.degree. C. or other temperatures that are suitable temperatures for cell metabolism. According to the materials of the cell, it may be made of cellulose polymers such as cellulose acetate, nitrocellulose and the like, or plastic, metal as well as various inorganic glasses.

A pump for supplying the substrate solution and antiseptic washing solution in the cell supplies the substrate solution flowing through the interior of the receptor molecule solid phase chip to make the living cell metabolism continue, and the interior of the receptor molecule solid phase chip is automatically washed with the substrate solution and antiseptic washing solution. Thus, washing of the interior of the receptor molecule solid phase chip and measurement can be carried out in one cell and, therefore, the apparatus for determination is simplified and measurement operations are also simplified.

A pump with a supplying rate of 1 to 1000 ml/h may be used, for example of a perista pump, a syringe pump and the like can be employed without particular limitations.

For determining the change of pH or oxygen consumption or glucose consumption from metabolism of specific living cells, a culture solution containing a substrate that can induce a change of pH or oxygen consumption or glucose consumption from metabolism of specific living cells may be used as a substrate solution. As the substrate, sugars such as glucose, fructose, sucrose and the like are most generally used. In this case, a culture solution having weak buffering ability is preferably used so as to sharply change the pH via metabolism by the organism. In addition, an enzyme that can specifically react with carbon dioxide or oxygen or glucose, such as carbonic anhydrase or glucose oxidase, is added in substrate solution so as to magnify the signal of the change of pH or oxygen consumption or glucose consumption from metabolism of specific living cells.

In order to prevent pollution of the sensor and cell by samples such as whole blood and culture substrate, an antiseptic washing solution is supplied after measurement. Antiseptic agents such as 2-phenoxyethanol, sodium azide and the like are most generally used.

The apparatus for the evaluation (observation) of specific living cells morphology and quantity consists of a light microscope and a microscope camera. After the above-mentioned measurement, the acceptor molecule solid phase chip is dyed by a cell stain such as Giemsa stain or Sternheimer-Malbin stain and the like. Under a light microscope, morphology and quantity of specific cells immobilized on the inner surface of acceptor molecule solid phase chip is observed carefully and a digital microscope photographs are also taken using a microscope camera in real time.

In addition, after dyeing the solid phase chip, color areas and quantity of color (stain) emission of all specific cells and one specific cell may be measured by a charge coupled device. Therefore, quantity of the specific cells can be calculated easily.

Further, all of the above-mentioned apparatuses including an apparatus for a bio-specific recognition reaction between specific living cells and a receptor molecule solid phase chip, an apparatus for the determination of activity and quantity of specific living cells and an apparatus for evaluation (observation) of specific living cells morphology may be unified to an automatic apparatus so as to further simplify all measurement operations.

In addition to specific living eukaryotic cells, bacterium, microorganism, and organelles such as mitochondria and the like may also be measured by this method. In this case, a substrate solution to be supplied in the cell is selected depending upon the subject to be determined.

A method for determination employing the present apparatus is described as follows:

A normal sample solution such as a cell soliquoid is first challenged with the receptor molecule solid phase chip and allowed to stand for a constant period of time. However, when the sample contains whole blood, a sample solution is supplied throwing the receptor molecule solid phase chip with a low speed so as to prevent corpuscle subsidence.

Then, after the bio-specific recognition reaction is completed, the receptor molecule solid phase chip is inserted into the cell. Alternatively, an operation of insertion of the receptor molecule solid phase chip in the cell may be automated by separately disposing a means for accommodating the receptor molecule solid phase chip.

With the receptor molecule solid phase chip accommodated in the cell as described above, a substrate solution is supplied in the cell from a liquid reservoir by the supplying pump. The substrate solution supplied in the cell flows from the lower to the upper part in the receptor molecule solid phase chip and is discharged through the outlet of the cell.

When the substrate solution is sufficiently supplied and washing of the interior of the receptor molecule solid phase chip is completed, supplying solution is completed. The measurement cell and the receptor molecule solid phase chip are filled with a substrate solution and the the metabolism reaction of living cells is generated. Thereafter, the solution in the receptor molecule solid phase chip is moved to the sensitive part of a sensor by a pump for feeding solution, and a change of pH or oxygen consumption or glucose consumption from the metabolism of the specific living cells is measured.

Analyzing these changes from the metabolism of the specific living cells with a special soft (least square method, peak area method and etc), the activity and quantity of living cells to be determined accurately and quickly.

After measurement is completed, the receptor molecule solid phase chip is removed from the cell and an antiseptic washing solution is supplied in the cell from the liquid reservoir by the supplying pump. Thus, the interior of the cell is automatically washed.

Finally, after dyeing the receptor molecule solid phase chip, the morphology and quantity of specific cells immobilized on the inner surface of acceptor molecule solid phase chip is observed carefully with a light microscope and a microscope camera or another apparatus.

The following experiments are provided for purposes of illustration and not for limitation Experiments Experiment 1

Measurement of Human CD4+ Lymphocyte Activity

1. Manufacture of a Receptor Solid Phase Chip

A glass capillary (33 mm long, 0.65 diameter purchased from Hirschmann Laborgerate Company in Germany) was soaked in 5% nitric acid aqueous solution and treated therein at 85.degree. C. for 90 minutes. Then, it was washed with pure water in an ultrasonic bath for 10 minutes so as to clean the inner surface of dust. Finally, it was soaked in pure water, in order to be made into a receptor solid phase chip.

The cleaned glass capillary was soaked in a polyethyleneimine solution (220 mg in 10 ml $H_2O$) for 30 minutes at room temperature. Then, it was washed with water 10 times by wicking action and carefully dried with nitrogen gas. It was subsequently soaked in polystyrene sulfonate sodium salt solution (200 mg in 10 ml 2M NaCl aqueous solution) for 20 minutes and washed with water 10 times and carefully dried with nitrogen gas. Likewise, it was subsequently soaked in poly-L-lysine solution (200 mg in 10 ml 2M NaCl aqueous solution) for 20 minutes and washed with water 10 times and carefully dried with nitrogen gas. It was subsequently soaked in biotin N-hydroxysuccinimide (BNHS) solution (200 mg in 10 mil dimethylformamide add 50 l triethylamine as a pH adjuster) over night at room temperature. After being washed with water 10 times and carefully dried with nitrogen gas, the capillary was soaked in a PBS solution (pH 7.2) containing 100 g/ml of streptavidin for 30 minutes and washed with PBS solution (pH 7.2) 10 times. Finally, it was soaked in a PBS solution (pH 7.2) containing 50 g/ml biotinylated anti-human CD4 antibody (manufactured by IMMUNOTECH, clone 13B8.2) for 40 minutes and washed with PBS solution (pH 7.2) 10 times.

Figure 4:
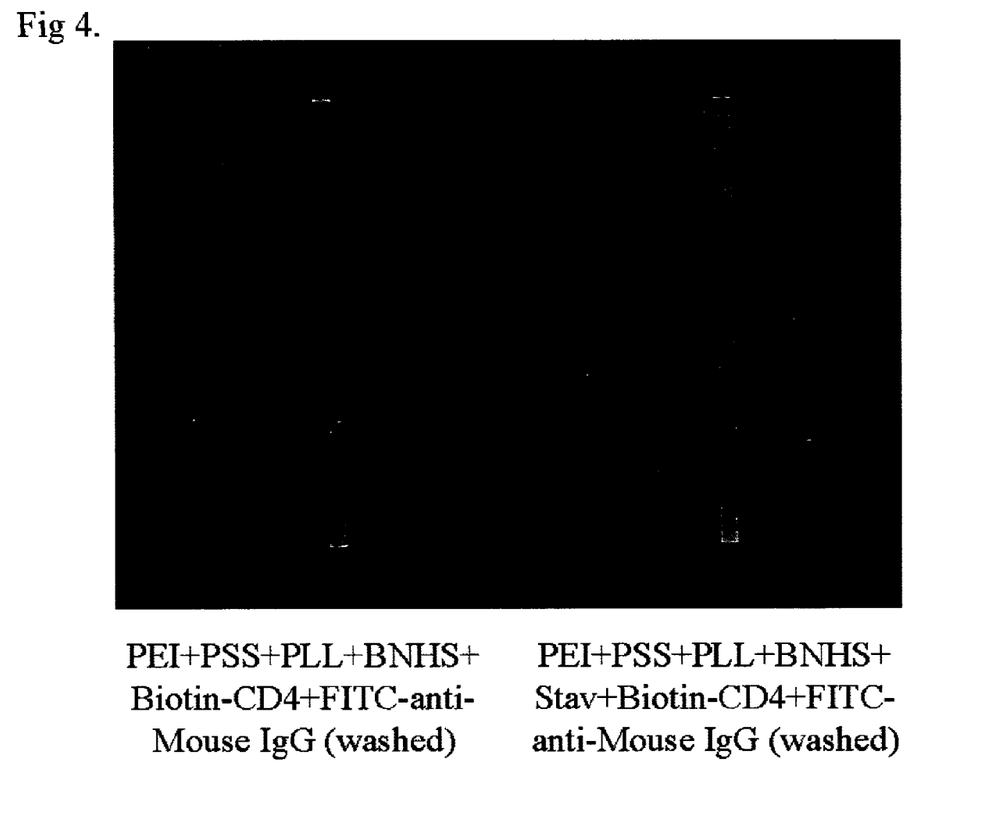
FIG. 4 show the relative fluorescence intensity versus wavelength for the measurement of the solid phase chip binding with FITC-labelled anti-Mouse IgG via fluorescence (right picture) versus a blank control (left picture) using UV transilluminator and a charge coupled device (CCD) camera as indicator.; (FITC is fluorescein isothiocyanate, stav+is streptavidin, PEI is polyehtyleneimine, and BNHS is biotin N hydroxysuccinimide)

For testing whether the anti-human CD4 antibody was immobilized on the inner surface of the present chip, the present antibody solid phase chip and a blank control chip that had only uncoated anti-human CD4 antibody were soaked in a PBS solution (pH 7.2) containing 50 g/ml FITC-labelled anti-Mouse IgG antibody (manufactured by SIGMA) for 40 minutes and washed with PBS solution (pH 7.2) 10 times. Thereafter, the present two chips were placed on a UV transilluminator (UV detection 480 nm) and the relative fluorescence intensity was detected by a charge coupled device (CCD) camera. The above-mentioned picture is shown in FIG. 4.

2. Measurement of Human CD4+ Lymphocyte Activity

This present antibody solid phase chip was connected with a perista pump by a rubber pipe (0.5 mm diameter, manufactured by NORTON) and 500 l venous blood from a healthy volunteer was sucked through challenging this chip with 15 l/min at room temperature. After all of the blood had being sucked through, this present chip was inserted into the cell of the measurement apparatus and a substrate solution was supplied in the cell using a perista pump to wash the interior of this present chip for 10 seconds. As a substrate solution, a (−)Hanks solution containing 10 mM ammonium chloride, 1 mM potassium bicarbonate, 0.5% glucose, 0.5 mM $Na_2CO_3$ and 0.1 mM carbonic anhydrase were prepared. Thereafter, the perista pump was stopped and 270 seconds later, 1l substrate solution in this chip was moved to the detection part of a pH sensitive field-effect transistor (pH-FET), wherein the detection part of the sensor was adjacent to the end of the present chip, and a change in the source potential was measured for 30 seconds at 37.degree. The present chip was subsequently removed from the cell, the perista pump was driven for 30 seconds to supply an antiseptic washing solution in the cell to wash the cell for the next measurement. For the antiseptic washing solution, an aqueous solution containing 0.1% sodium azide was prepared.

After the measurement was completed, the present chip was soaked in Sternheimer-Malbin stain solution for 10 minutes at room temperature. Under a light microscope, the morphology and quantity of human CD4+ lymphocyte cells immobilized on the inner surface of the present chip was observed carefully and digital microscope photographs were also taken using a microscope camera in real time.

3. Results

The same blood sample was continually measured two times by the present antibody solid phase chip under the same conditions. The results are described in the following table.

|  | Blank chip (n = 3) | The 1st time Of the antibody chip (n = 3) | The 2st time of the antibody chip (n = 3) |
|---|---|---|---|
| Mean activity | 0.02 mV | 23.71 mV | 22.98 mV |
| SD | ±0.013 | ±0.035 | ±0.028 |
| CV % | 0.126% | 0.204% | 0.169% |

Figure 5:
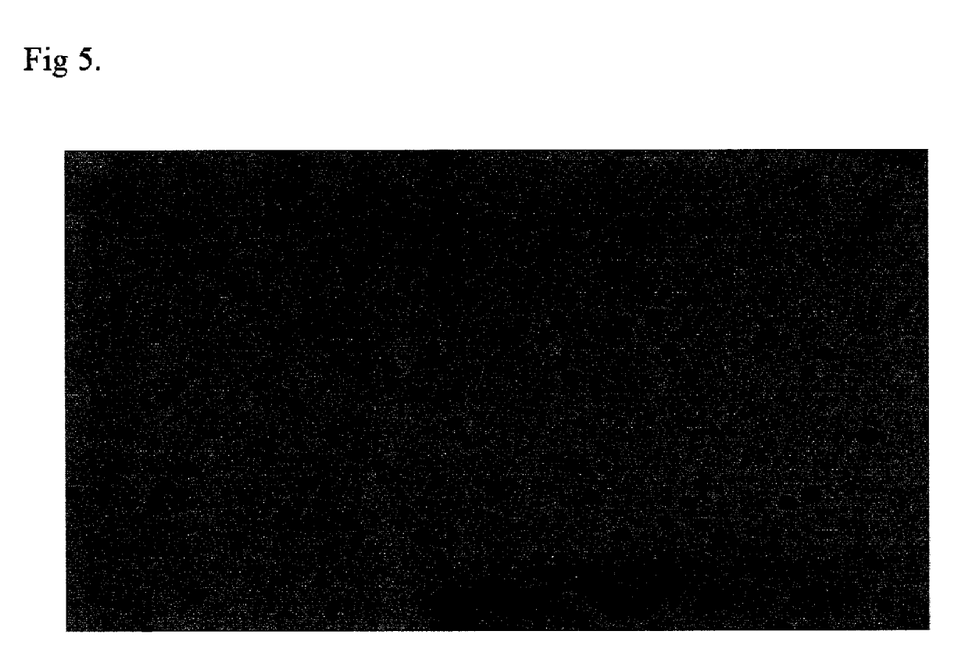
FIG. 5 is an image of a microscope photograph showing CD4+ lymphocyte that has been immobilized on the inner surface of the solid phase chip using whole blood of a health volunteer as sample.

As is apparent from the above table, the activity of human CD4+ lymphocyte cells can be selectively, quickly and continually measured with an excellent repeat using the present invention. Furthermore, as is shown in FIG. 5, morphology and quantity of human CD4+ lymphocyte cells can be clearly observed.

Experiment 2

The measurement of a change of human CD4+ lymphocyte activity after cells are subjected to SEA 1. Manufacture of a Receptor Solid Phase Chip was as Same as Experiment 1.

2. Measurement of a Change of Human CD4+ Lymphocyte Activity after Cells were Subjected to the SEA The process of the measurement was almost as same as experiment 1, however, in addition to the substrate solution used in experiment 1, a substrate solution containing 10 g/ml super enterotoxins antigen (SEA) was used.

3. Results

Figure 6:
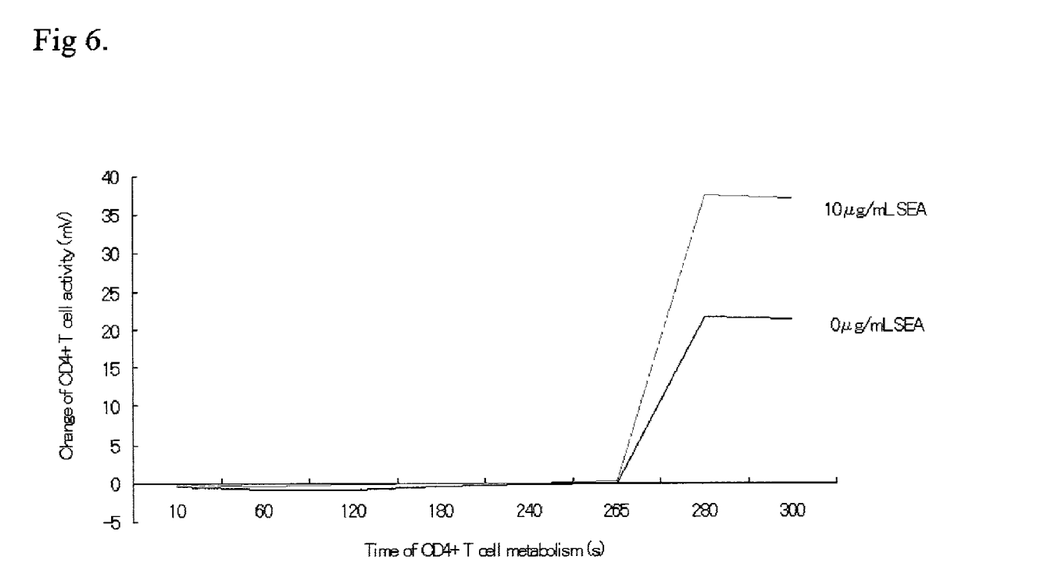
FIG. 6 is a graph showing the change of CD4+ lymphocyte activity from a health volunteer's whole blood using super enterotoxin antigen (SEA) as a irritant agent.

The measurement results are shown in FIG. 6. As is apparent from FIG. 6, a change of human CD4+ lymphocyte activity after cells are exposed to SEA can be measured easily and accurately using the present invention.

Experiment 3

The measurement of a change of human neutrophil activity when health condition of the subject person was different 1. Manufacture of a Receptor Solid Phase Chip Except for the receptor being changed to 50 g/ml biotinylated anti-mouse IgG antibody (manufactured by SIGMA), the process was as same experiment 1. There are Fc receptors on the surface of neutrophil, so anti-mouse IgG antibody that has Fc parts was used as a receptor to be immobilized on the surface of chip.

2. Measurement of a Change of Human Neutrophil Activity when Health Condition of the Subject Person was Different As a sample, venous blood drawn from the same person on different days was prepared. However, the health condition of the subject person on different days was different. Furthermore, the quantity of neutrophils in whole blood was measured by hemacytometer before the measurement. The other processes were the same as experiment 1.

3. Results

Figure 7:
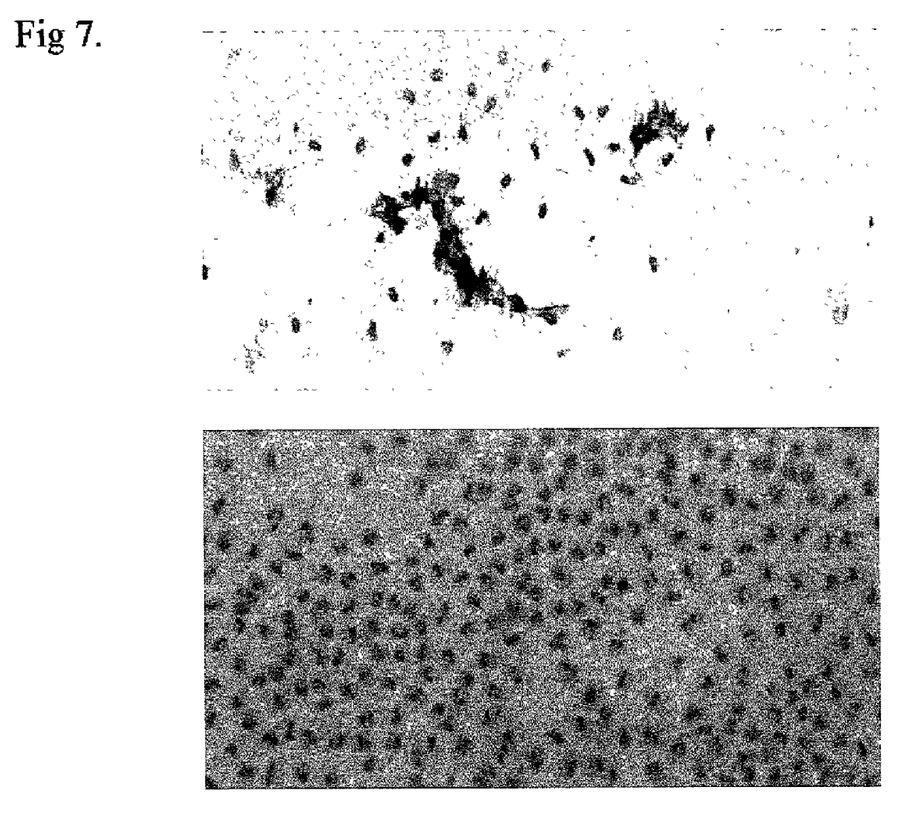
FIG. 7 is an image of a microscope photograph showing neutrophils from the same volunteer's whole blood that has been immobilized on the inner surface of the solid phase chip when the health condition was good (upper picture) and the health condition was not good (lower picture), however, the quantity of neutrophils was similar when measured by hemacytometer.
Figure 8:
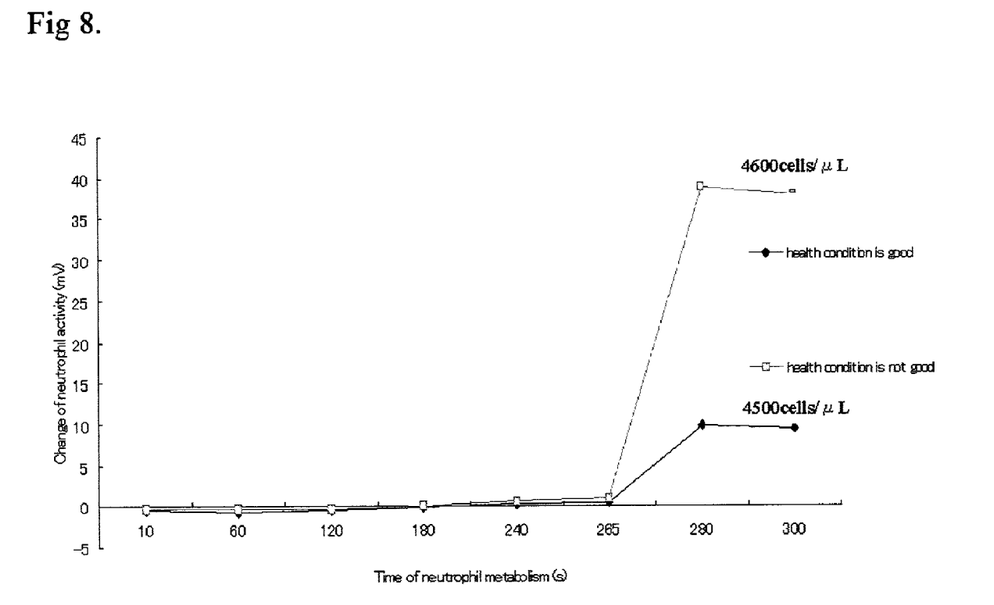
FIG. 8 is a graph showing the change of neutrophil activity according to FIG. 7.

The measurement results are shown in FIG. 7 and FIG. 8. When the health condition of the subject person is not good, the quantity of neutrophils in whole blood is not changed at first but the activity of neutrophils is already changed. Especially, Fc receptors are "irritated" so as to recognize and bind much more anti-mouse IgG antibody than when the health condition of the subject person is good. As is shown in FIG. 7, the quantity of neutrophil immobilized on the inner surface of the solid phase chip rose sharply, however, the quantity of neutrophil in whole blood was almost similar to each other. In addition, as is apparent from FIG. 8, a change of human neutrophil activity when the health condition of the subject person was changed can be measured easily and sensitively using the present invention. This means the present invention may be a novel method for early clinical diagnosis.

While presently preferred embodiments have been described for the purposes of the disclosure, numerous changes in the arrangement, methods, steps and apparatus parts can be made by those skilled in the art. Such changes are encompassed within the spirit of the invention by the appended claims.

I claim:

1. A method for obtaining at least one measurement of cellular metabolism of at least one specific living cell or at least one specific organelle in a sample, comprising the steps of:
   a) providing a binder comprising:
      (i) a planar flat-surfaced solid substrate comprised of quartz glass;
      (ii) polyionic layers comprising an alternating arrangement of at least one polyanion layer and at least one polycation layer coated on and substantially parallel to the surface of said planar flat-surfaced solid substrate; and
      (iii) at least one antibody or antibody fragment, affixed to the outermost of said polyionic layers and capable of binding a specific molecule located on said at least one specific living cell or said at least one specific organelle;
   b) providing a sample suspected of containing said at least one specific living cell or said at least one specific organelle;
   c) contacting said sample with said binder;
   d) incubating said sample and said binder under conditions that allow said antibody or antibody fragment to bind said specific molecule, thereby immobilizing said at least one specific living cell or said at least one specific organelle;
   e) providing a culture solution containing a substrate that can induce cellular metabolism;
   f) contacting said culture solution with said immobilized at least one specific living cell or said immobilized at least one specific organelle; and
   g) measuring change of pH of said culture solution to measure cellular metabolism.

2. The method of claim 1, wherein said planar flat-surfaced solid substrate is configured to comprises a capillary.

3. The method of claim 1, wherein said at least one antibody or antibody fragment is affixed to the outermost of said polyionic layers by covalent binding.

4. The method of claim 1, wherein said at least one antibody or antibody fragment is affixed to the outermost of said polyionic layers by non-covalent binding.

5. The method of claim 1, wherein said at least one antibody or antibody fragment is affixed to the outermost of said polyionic layers by biotin-avidin binding.

6. The method of claim 1, wherein said at least one antibody or antibody fragment is affixed to the outermost of said polyionic layers by aminosilane coupling.

7. The method of claim 1, wherein said sample comprises whole blood.

8. The method of claim 1, wherein said at least one specific living cell comprises a T-lymphocyte.

9. The method of claim 8, wherein said T-lymphocyte comprises a CD4+ T-lymphocyte.

10. The method of claim 1, wherein said specific molecule comprises a CD antigen.

11. The method of claim 10, wherein said CD antigen comprises a CD4 antigen.

12. The method of claim 1, further comprising pumping at least one solution selected from a sample solution, a wash solution, a reagent solution, a substrate solution, a labelling solution, and a combination thereof.

13. The method of claim 1, wherein the change of pH of said culture solution is measured with a pH sensitive field-effect transistor (pH-FET).

14. The method of claim 1, further comprising observing said immobilized at least one specific living cell or said immobilized at least one specific organelle under a microscope.

* * * * *